US010400582B2

(12) United States Patent
Burks et al.

(10) Patent No.: US 10,400,582 B2
(45) Date of Patent: *Sep. 3, 2019

(54) MULTIPLE WELL GRAVITY-ASSISTED COLUMN FLOW TESTING

(71) Applicant: Halliburton Energy Services, Inc., Houston, TX (US)

(72) Inventors: Jody M Burks, Houston, TX (US); Kristina M Henkel, Houston, TX (US); Denise Nicole Benoit, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 26 days.

This patent is subject to a terminal disclaimer.

(21) Appl. No.: 15/036,668

(22) PCT Filed: Aug. 20, 2014

(86) PCT No.: PCT/US2014/051896
§ 371 (c)(1),
(2) Date: May 13, 2016

(87) PCT Pub. No.: WO2015/147905
PCT Pub. Date: Oct. 1, 2015

(65) Prior Publication Data
US 2016/0290909 A1    Oct. 6, 2016

Related U.S. Application Data

(63) Continuation-in-part of application No. PCT/US2014/032262, filed on Mar. 28, 2014.

(51) Int. Cl.
*G01N 11/06* (2006.01)
*E21B 47/10* (2012.01)
*G01N 33/28* (2006.01)

(52) U.S. Cl.
CPC ............. *E21B 47/10* (2013.01); *G01N 11/06* (2013.01); *G01N 33/2823* (2013.01)

(58) Field of Classification Search
None
See application file for complete search history.

(56) References Cited

U.S. PATENT DOCUMENTS

| 5,591,118 A | 1/1997 | Bierck |
| 2002/0110925 A1 | 8/2002 | Mansky et al. |

(Continued)

FOREIGN PATENT DOCUMENTS

| WO | WO-2013076242 A2 | 5/2013 |
| WO | 2015147880 | 10/2015 |

(Continued)

OTHER PUBLICATIONS

"International Application Serial No. PCT/US2014/051893, International Search Report dated Dec. 22, 2014", 3 pgs.

(Continued)

*Primary Examiner* — Jill E Culler
(74) *Attorney, Agent, or Firm* — Chamberlain Hrdlicka

(57) ABSTRACT

A method of flow testing can include dispensing at least one solid material and at least one liquid into each of multiple wells in a filter plate, and allowing the liquid to flow from the filter plate only by force of gravity. A flow testing system can include a multiple well filter plate, each of the wells having disposed therein a selected combination of formation particles, a fracturing fluid composition and a liquid hydrocarbon, and a collection plate vertically below the filter plate. The fracturing fluid composition and the liquid hydrocarbon flow from the filter plate to the collection plate only by force of gravity.

20 Claims, 7 Drawing Sheets

(56) References Cited

U.S. PATENT DOCUMENTS

| | | | |
|---|---|---|---|
| 2008/0020944 A1 | 1/2008 | Anderson et al. | |
| 2010/0139914 A1 | 6/2010 | Tehrani et al. | |
| 2014/0319080 A1* | 10/2014 | Kaarigstad | E21B 49/00 210/774 |

FOREIGN PATENT DOCUMENTS

| | | |
|---|---|---|
| WO | WO-2015147904 A1 | 10/2015 |
| WO | WO-2015147905 A1 | 10/2015 |

OTHER PUBLICATIONS

"International Application Serial No. PCT/US2014/051893, Written Opinion dated Dec. 22, 2014", 7pgs.
"International Application Serial No. PCT/US2014/051896, International Search Report dated Dec. 22, 2014", 3 pgs.
"International Application Serial No. PCT/US2014/051896, Written Opinion dated Dec. 22, 2014", 9 pgs.
Anonymous, "Swing Powerdose," Chemspeed Technologies, retrieved Oct. 11, 2018: pp. 1-3, <https://www.chemspeed.com/swing-powderdose/>.
Anonymous, "VolumeCheck 50 & 100 Factsheet," BioMicroLab, Inc., retrieved Sep. 28, 2018: pp. 1-2, <http://www.biomicrolab.com/volume-detection/volume-check>.
Anonymous, "VolumeCheck 100 Product Presentation," BioMicroLab, Inc., retrieved Sep. 28, 2018: pp. 1-22.
Penny et al., SPE 154308: "Nanofluid System Improves Post Frac Oil and Gas Recovery in Hydrocarbon Rich Gas Reservoirs," SPE International, 2012: pp. 1-18.
Penny et al., SPE 159692: "Laboratory and Field Evaluation of Proppants and Surfactants used in Fracturing of Hydrocarbon Rich Gas Reservoirs," SPE International, 2012: pp. 1-23.

* cited by examiner

MULTIPLE WELL GRAVITY-ASSISTED COLUMN FLOW TESTING

PRIORITY APPLICATIONS

This application is a U.S. National Stage Filing under 35 U.S.C. 371 from. International Application No. PCT/US2014/051896, filed on 20 Aug. 2014, and published as WO 2015/147905 Al on 1 Oct. 2015, which application claims priority to International Application No. PCT/US2014/032262, filed on 28 Mar. 2014, which applications and publication are incorporated herein by eference in their entirety.

TECHNICAL FIELD

This disclosure relates generally to equipment utilized and operations performed in conjunction with a subterranean well and, in one example described below, more particularly provides for column flow testing in which flow is by gravity through multiple columns in a multiple well plate.

BACKGROUND

It can be useful to determine how readily fluids (such as, hydrocarbons, fracturing fluids, etc.) flow through earth formations and proppant. For example, selection of a fracturing fluid composition can be informed by knowledge of how various fracturing fluid compositions affect flow of hydrocarbons through earth formations and/or proppant. Therefore, it will be appreciated that improvements are continually needed in the art of flow testing.

DETAILED DESCRIPTION

Figure 1:
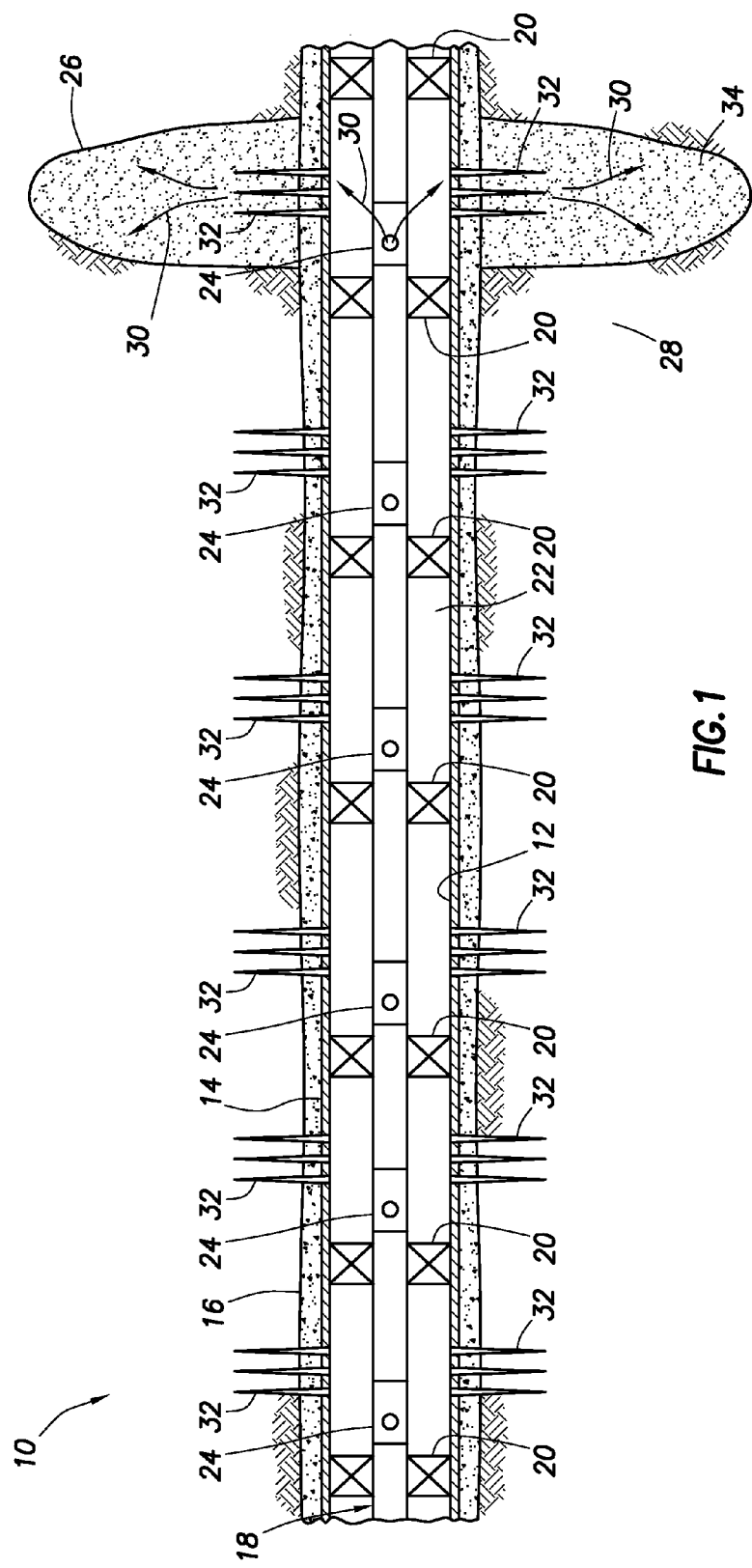
FIG. 1 is a representative partially cross-sectional view of a well system and associated method for which principles of this disclosure can be of use.

Representatively illustrated in FIG. 1 is a well system 10 and associated method which can benefit from the principles of this disclosure. However, it should be clearly understood that the system 10 and method are merely one example of an application of the principles of this disclosure in practice, and a wide variety of other examples are possible. Therefore, the scope of this disclosure is not limited at all to the details of the system 10 and method described herein and/or depicted in the drawings.

In the FIG. 1 system 10, a generally horizontal wellbore 12 is lined with casing 14 and cement 16. However, it should be clearly understood that it is not necessary for any particular wellbore section to be generally horizontal, or for the wellbore section to be cased or cemented.

In the FIG. 1 example, a generally tubular completion or stimulation string 18 is positioned in the wellbore 12 and packers 20 are set, to thereby isolate separate sections of an annulus 22 formed radially between the tubular string and the wellbore 12. Flow control devices 24 (such as, sliding sleeve valves, crossovers, specialized "frac" valves, etc.) selectively permit and prevent flow between an interior of the tubular string 18 and the annulus 22.

In other examples, the flow control devices 24 could be incorporated into the casing 12, packers 20 may not be used to isolate separate sections of the annulus 22, etc. Thus, it will be appreciated that the scope of this disclosure is not limited to use of any particular components, or combination of components, of the system 10 depicted in FIG. 1 or described herein.

A fracture 26 is formed in an earth formation 28 penetrated by the wellbore 12. The fracture 26 is formed by flowing pressurized fracturing fluid 30 outward from the tubular string 18, into the annulus 22 between an adjacent pair of the packers 20, and then into the formation 28 via perforations 32 formed through the casing 14 and cement 16.

Although only one fracture 26 is depicted in FIG. 1, multiple fractures can be formed at multiple locations along the wellbore 12 by, for example, selectively opening the flow control devices 24 and flowing the fracturing fluid 30 into the formation 28. The multiple locations can correspond to multiple different zones of the formation 28, or they can correspond to different formations or lithologies penetrated by the wellbore 12. Different fracturing fluid 30 compositions may be used at the different fracture locations along the wellbore 12.

Proppant 34 can be flowed into the fracture 26 along with the fracturing fluid 30, in order to prop the fracture open after it has been formed. The proppant 34 can serve purposes in addition to propping the fracture 26 open, such as, serving as a filter to prevent production of formation fines.

The proppant 34 can be a naturally-occurring substance (such as, sand), or a manufactured or synthesized substance (such as, glass beads, polymer spheres or fibers, etc.). Thus, the scope of this disclosure is not limited to any particular purpose or composition of the proppant 34 and, indeed, is not limited to use of any proppant at all.

It is desired, in this example, to determine how the fracturing fluid 30 flowed into the formation 28 affects subsequent flow of fluids (such as, formation water and/or formation hydrocarbons) through the formation and the proppant 34. In addition, it is desired to determine the amount of the fracturing fluid 30 itself that flows through the formation 28 and the proppant 34. In this way, an intelligent choice can be made as to a particular composition of the fracturing fluid 30 to use for each formation 28 or zone to be fractured.

The fracturing fluid 30 can be a combination of a variety of different components. For example, the fracturing fluid 30 can include water, a surfactant, a gel, a biocide, a clay stabilizer, a gel breaker, and/or other components. These components can be combined in various ratios. Thus, it will be appreciated that it would be very time-consuming to individually test each possible fracturing fluid 30 composition to determine its suitability for use with each formation 28 lithology and mineralogy, each proppant 34, each formation fluid, etc.

Instead, examples of systems and methods described herein allow for simultaneously flow testing a large number of fracturing fluid, formation, proppant and/or formation fluid combinations, so that informed decisions regarding choice of fracturing fluid composition can be made relatively rapidly. In addition, these systems and methods can be readily computer-controlled and automated, so that pertinent flow test results can be quickly made available to decision-makers, and possibilities for human error are minimized.

Figure 2:
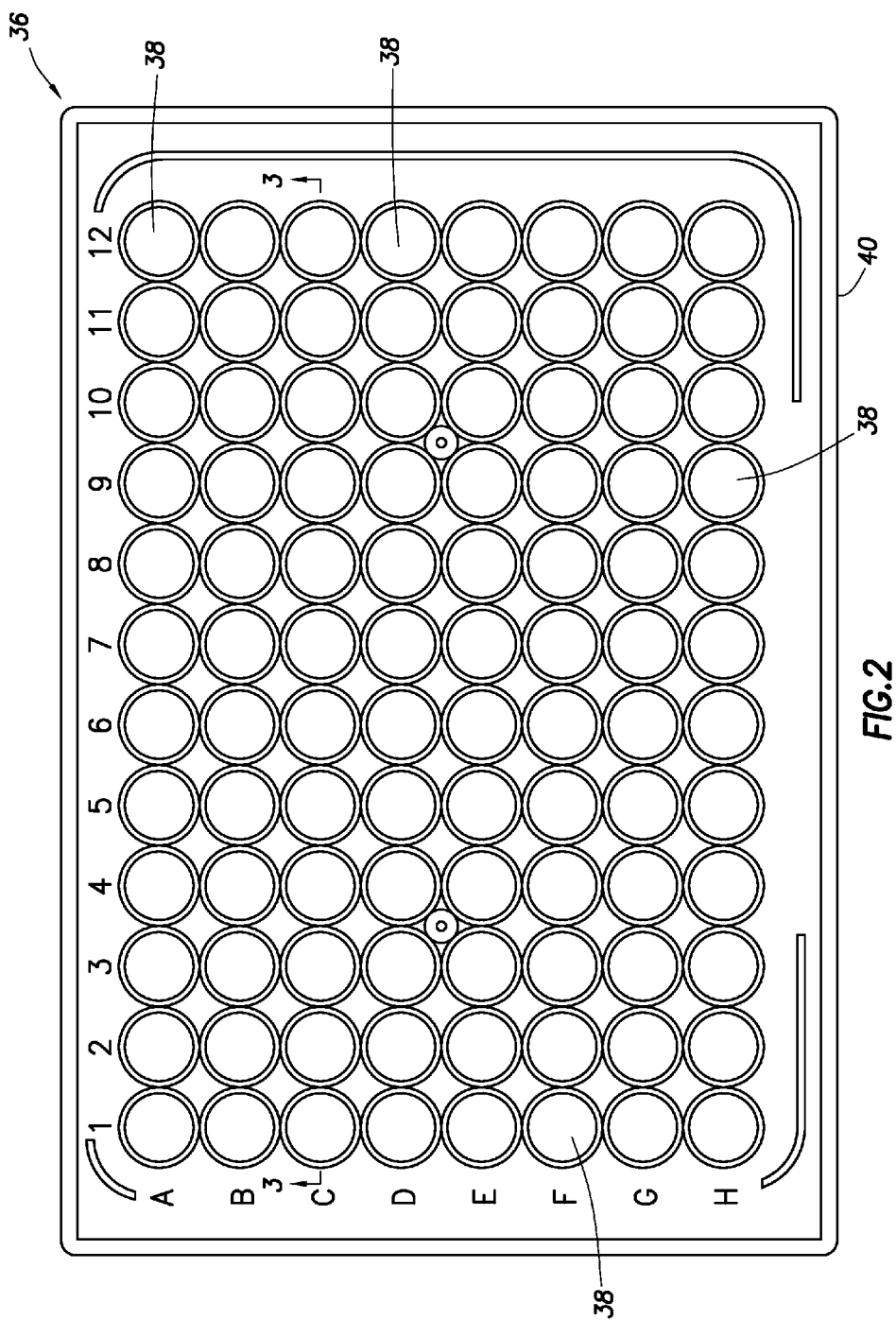
FIG. 2 is a representative top view of an example of a multiple well filter plate that can be used in systems and methods embodying the principles of this disclosure.

Referring additionally now to FIG. 2, an example of a filter plate 36 that can be used in systems and methods described below is representatively illustrated. A top view of the filter plate 36 is depicted in FIG. 2.

In the FIG. 2 example, the filter plate 36 includes ninety-six wells 38 arranged in eight rows and twelve columns. In other examples, six, twenty-four or over a hundred wells 38 could be included in the filter plate 36. Thus, it should be clearly understood that the scope of this disclosure is not limited to use of any particular number of wells in a filter plate.

The wells 38 comprise receptacles for various formation solids, proppants, formation fluids, flowback water, fracturing fluids, etc., to be flow tested. In this manner, a large number and variety of different combinations and ratios can be simultaneously tested.

For example, using the filter plate 36 with ninety-six wells 38 as depicted in FIG. 2, each well could be loaded with the same formation particles (e.g., cuttings retrieved while the formation is being drilled) and/or proppant, and twelve different fracturing fluid compositions (e.g., with different surfactants or surfactant ratios, and with a zero surfactant control) could be flow tested with eight repetitions on the same plate to identify an optimal surfactant or surfactant ratio. As another example, each well 38 could be loaded with the same formation particles and/or proppant, and ninety-six different combinations of two or more surfactants in a blend could be flow tested on the same plate. As another example, each well 38 could be loaded with the same formation particles and/or proppant, and ninety-six different combinations of two or more surfactant blends could be flow tested on the same plate. As yet another example, each well 38 could be loaded with the same formation particles and/or proppant, and ninety-six different combinations of fracturing fluid components could be flow tested to identify detrimental factors (such as, incompatibilities between components that may or may not depend on the specific mineralogy of the formation).

Thus, it will be appreciated that a variety of different combinations can be simultaneously tested using the filter plate 36 with multiple wells 38. Note that the wells 38 can be integrally formed with a support structure 40 of the filter plate 36, or the wells could be separable from the support structure.

Figure 3:
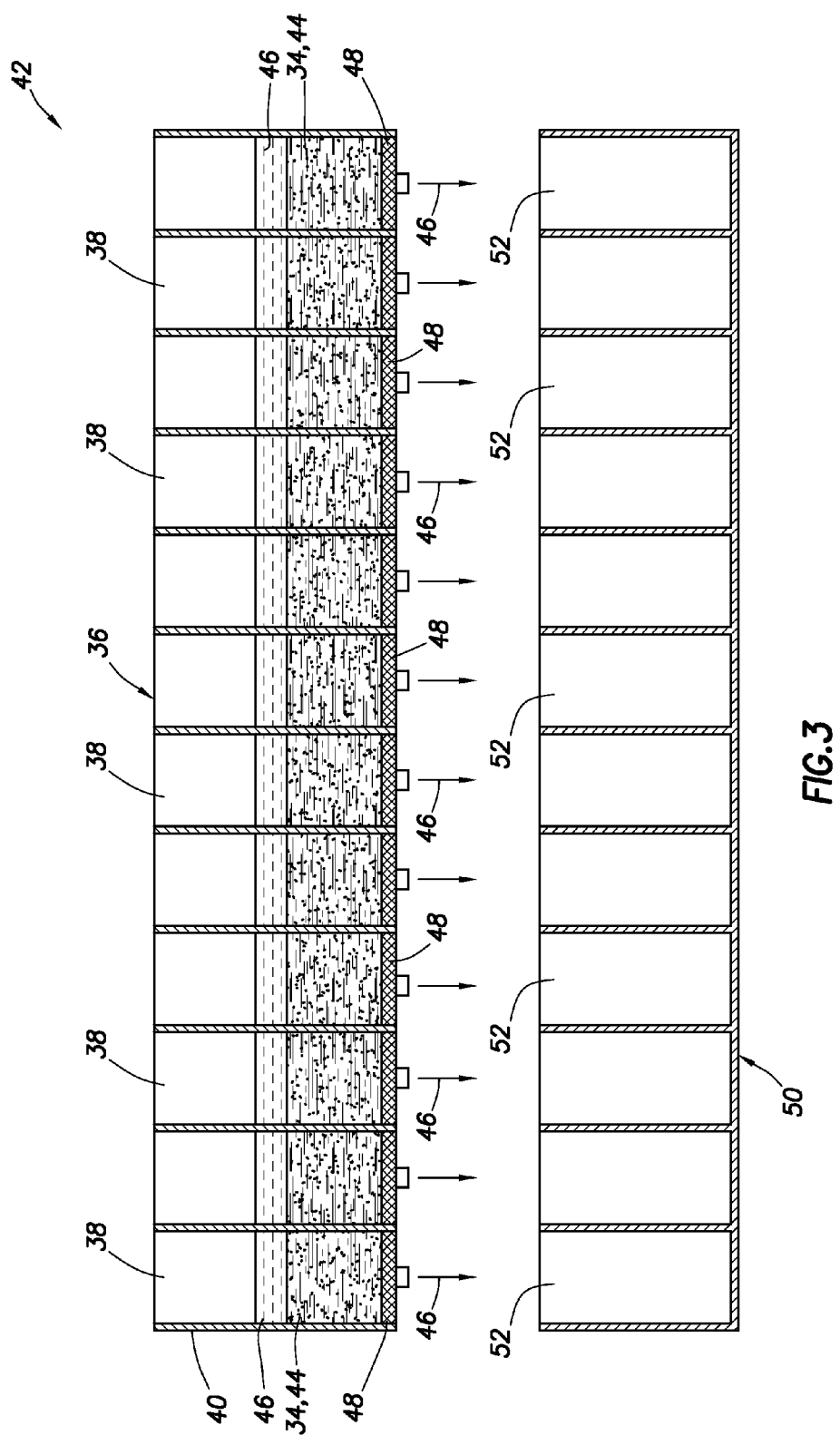
FIG. 3 is a representative cross-sectional view of the multiple well filter plate of FIG. 2, taken along line 3-3 of FIG. 2.

Referring additionally now to FIG. 3, a cross-sectional view of the filter plate 36 is representatively illustrated, taken along line 3-3 of FIG. 2. In this view, the filter plate 36 is depicted as being part of a flow testing system 42 that can embody the principles of this disclosure.

In the FIG. 3 example, a solid material (such as, formation particles 44 and/or proppant 34) and a liquid 46 (such as, formation water or a 7% potassium chloride solution) are dispensed into each of the wells 38. Prior to loading the wells 38 with the solid material, a porous ceramic or screen 48 can be placed at a bottom of each well to prevent the solid material from falling out of the well. Optionally, prior to loading the wells 38 with the liquid 46, a sealing device 54 (such as, a sealing mat, PARAFILM™, sealing tape or other sealing material, not shown in FIG. 3, see FIG. 4) can be used to prevent the liquid from flowing out of the wells.

The liquid 46 is allowed to flow through the solid material and into a collection plate 50. This flow can be by force of gravity, and/or the flow may be vacuum-assisted or by centrifugation. Once the liquid 46 has completed flowing from the filter plate 36 to the collection plate 50, the filter plate 36 and columns of solid materials in the wells 38 are ready for further flow testing.

In some examples, the liquid 46 can comprise flowback water (e.g., produced fracturing fluid), in which case it may be useful for the collection plate 50 to include separate wells 52 corresponding to the respective wells 38 in the filter plate 36, so that a volume or mass of liquid flowed from each well 38 can be determined. In this manner, a volume or mass of the liquid 46 retained in each of the wells 38 can be determined.

Figure 4:
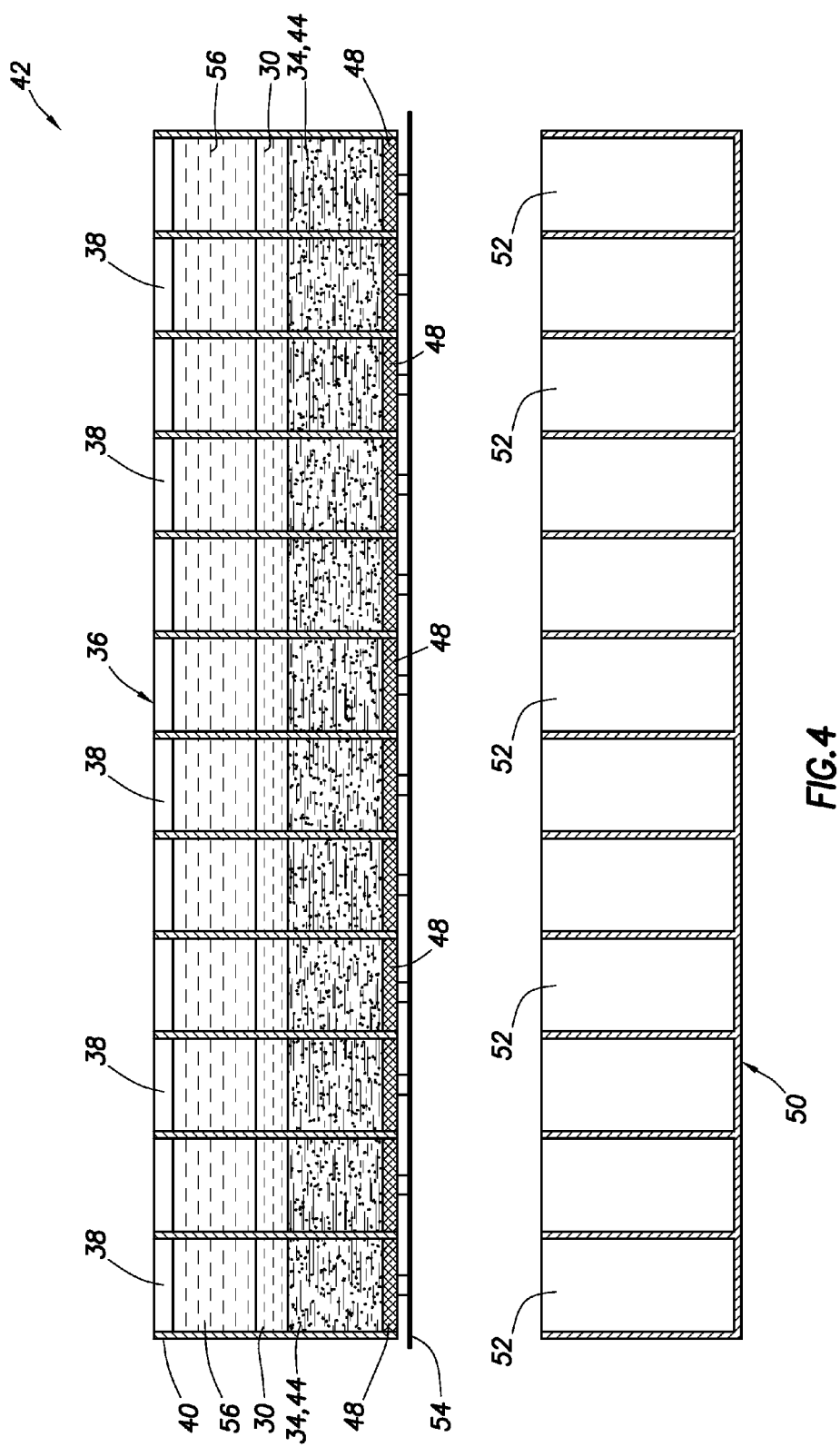
FIG. 4 is a representative cross-sectional view of the multiple well filter plate having solid materials and fluids loaded therein.

Referring additionally now to FIG. 4, the system 42 is representatively illustrated after further liquids have been dispensed into the wells 38 in the filter plate 36. In this example, fracturing fluid 30 and liquid formation hydrocarbons 56 (such as, crude oil, gas condensate, etc.) are dispensed into the wells 38. The sealing device 54 temporarily prevents the liquids from flowing out of the filter plate 36.

The collection plate 50 is depicted in FIG. 4 as being the same as that used in FIG. 3. However, a different type or configuration of the collection plate 50 may be used, if desired.

Figure 5:
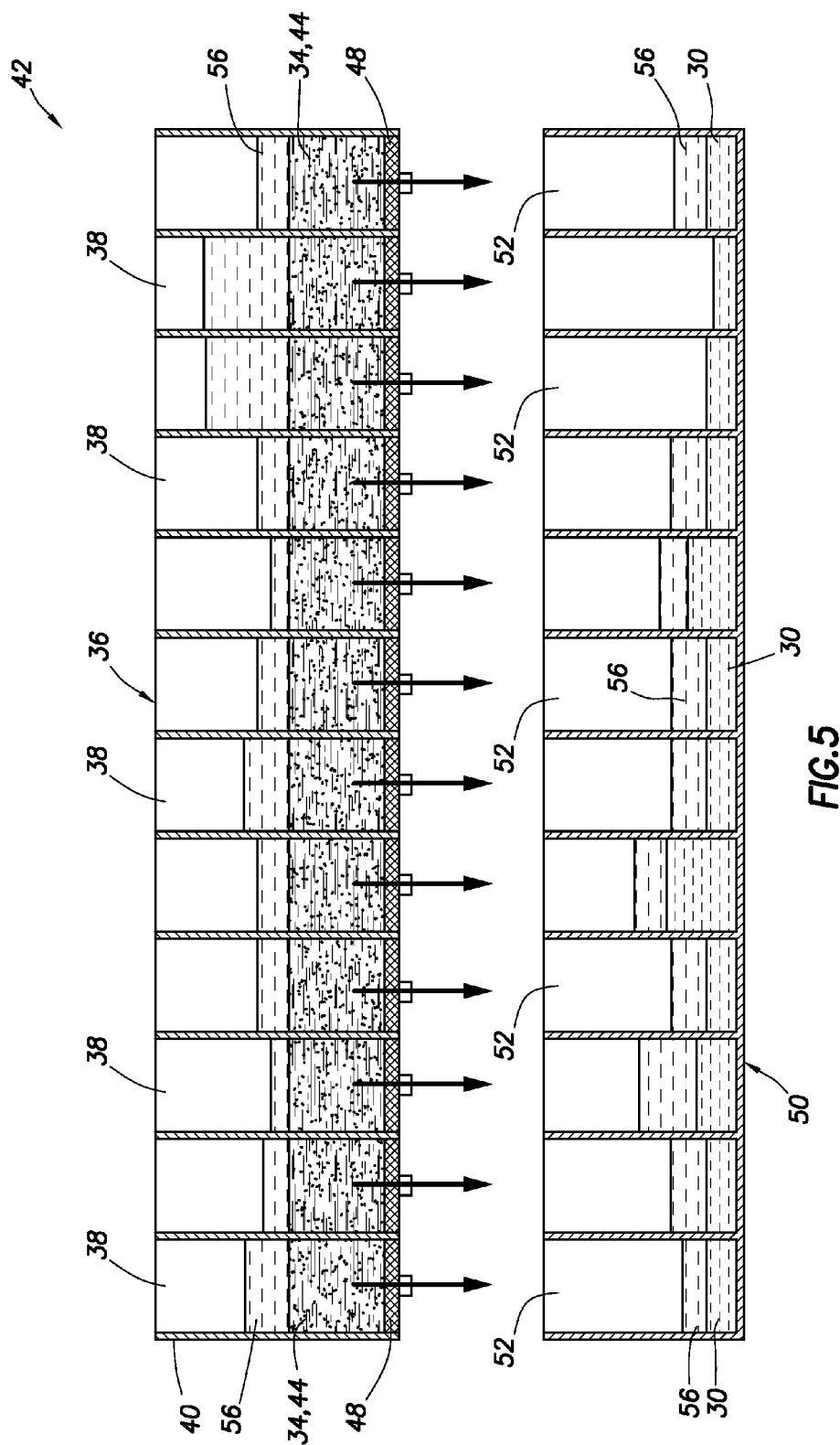
FIG. 5 is a representative cross-sectional view of the multiple well filter plate during a flow test.

Referring additionally now to FIG. 5, the system 42 is representatively illustrated after the sealing device 54 has been removed. The liquids (in this example, fracturing fluid 30 and formation hydrocarbons 56) are now allowed to flow from the filter plate 36 to the collection plate 50. A hydrophobic or hydrophilic layer (not shown) may be used in the wells 52 of the collection plate 50 to separate the fracturing fluid 30 from the hydrocarbons 56, so that these components can be separately measured if desired.

In this example, the liquids flow from the filter plate 36 only by force of gravity. Vacuum or centrifugation is not used to assist with the flow of the liquids.

One benefit of flowing the liquids from the filter plate 36 only by force of gravity is that, at multiple times during the flow test, a volume or mass of the liquids collected in the collection plate 50 can be measured. This allows for monitoring of non-linear flows (e.g., where a flow rate of the liquids changes over time).

Another benefit of flowing the liquids from the filter plate 36 only by force of gravity is that a point at which breakthrough of the formation hydrocarbons 56 from each of the wells 38 occurs can be identified. For example, each time a volume or mass of the liquids collected in the collection plate 50 is measured, an ultraviolet spectrometer (such as, an ultraviolet-visible (UV-VIS) spectrometer) or other suitable instrument can be used to scan the wells 52 and detect whether the hydrocarbons 56 are present in any of the wells.

Figure 6:
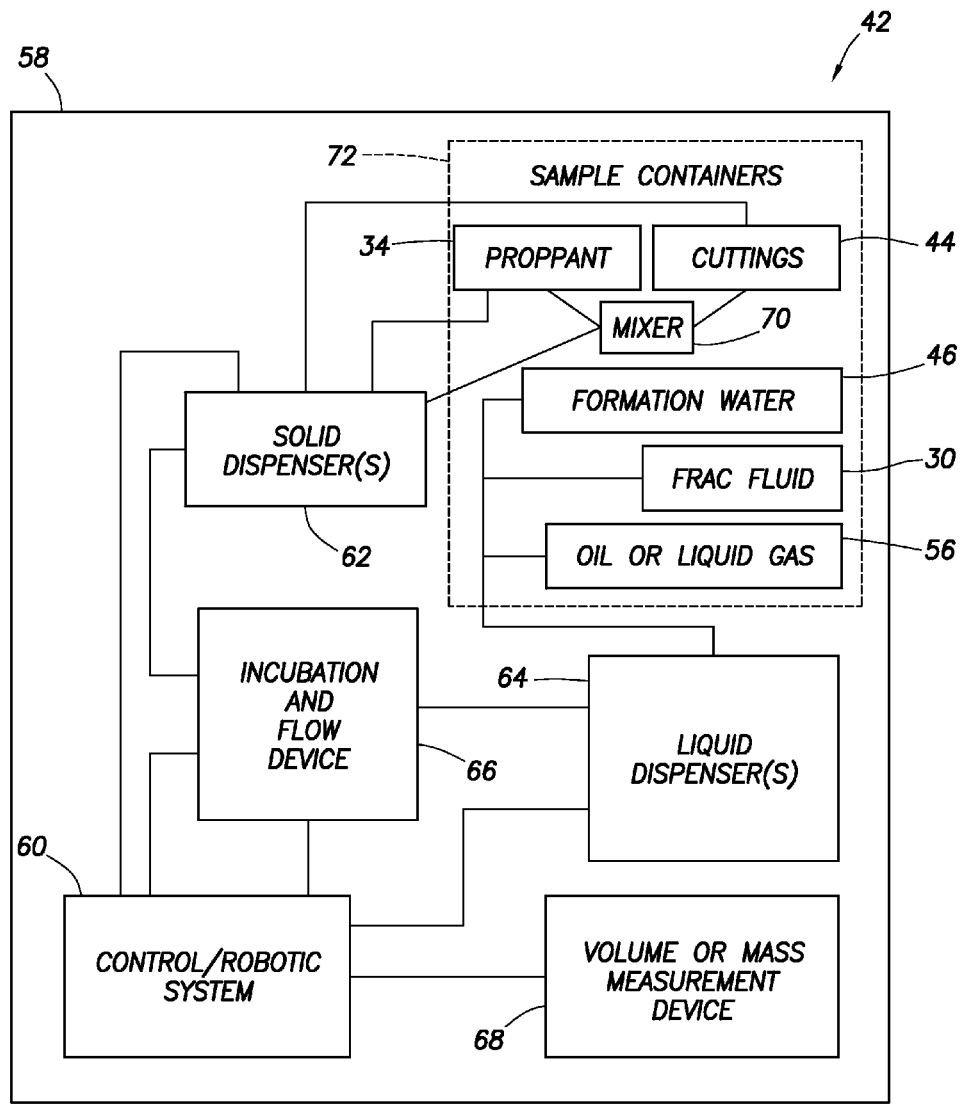
FIG. 6 is a representative block diagram of an example flow testing system that can embody the principles of this disclosure.

Referring additionally now to FIG. 6, a block diagram of one example of the system 42 is representatively illustrated. In this example, various components of the system 42 are contained in a single enclosure 58 for convenient transport, installation, operation, etc. However, in other examples, the components of the system 42 may not be contained in a single enclosure, and external devices (such as, input devices, monitors, printers, storage devices, etc.) may be included in the system. Thus, the scope of this disclosure is not limited to the details of the system 42 example as depicted in FIG. 6 or described herein.

In the FIG. 6 example, the system 42 includes a control system 60 that can be used to control operation of various robotic or automated devices of the system. For example, the system 42 can include one or more solids dispensers 62 and/or one or more liquids dispensers 64 that are capable of dispensing the solid materials (such as, formation particles 44 and proppant 34) and liquids (such as, liquid 46, fracturing fluid 30, and hydrocarbons 56) in selected combinations and ratios into the wells 38 of the filter plate 36 (not shown in FIG. 6, see FIG. 2).

The FIG. 6 example of the system 42 also includes an automated incubation and flow device 66 for containing and manipulating the filter plate 36 and collection plate 50. Multiple filter plates 36 and collection plates 50 can be contained and manipulated by the device 66 in some examples.

The FIG. 6 example of the system 42 also includes an automated volume or mass measurement device 68. The device 68 is used to measure a volume and/or mass of liquids collected in each well 52 of the collection plate 50 (not shown in FIG. 6, see FIGS. 3-5). The system 42 can also include an automated analytical or detection device (such as but not limited to, an automated UV-VIS spectrometer) for determining whether formation hydrocarbons 56 are present in any of the wells 52.

A mixer 70 may be used to mix the solid materials prior to the dispenser 62 dispensing the solid materials into the filter plate 36. However, in some examples, mixing of solid materials may be unnecessary or undesired.

Suitable automated robotic solids and liquids dispensing equipment is available from Chemspeed Technologies of Switzerland, and North Brunswick, N.J. USA, and York, United Kingdom. Suitable automated ultrasonic liquid level detection equipment is available from BioMicroLab, Inc. of Concord, Calif. USA.

To aid in simulating downhole conditions for the flow tests, the entire system 42 or selected components thereof may be placed in an oven, or one or more heating devices (such as, a plate heater, heated dispensers 62, 64, etc.) can be incorporated into the system. In one example, sample containers 72 containing the various solid and liquid materials can be heated to downhole temperature prior to being dispensed into the filter plate 36, and the filter plate can be heated during incubation or at least prior to and/or during the flow tests, in order to ensure that all materials have equilibrated to downhole temperature.

The control system 60 controls operation of the dispensers 62, 64, the flow device 66, the measurement device 68 and any heating equipment (not shown). The control system 60 can include at least one processor, one or more types of memory, input and output devices, programmed instructions and/or other computer features.

It is contemplated that the system 42 could be sufficiently automated that an operator can simply load the sample containers 72 with appropriate solid and liquid materials, use an input device (not shown) to input various pertinent parameters (such as, downhole temperature, types of tests to be performed, etc.), and the system can then perform the tests without further human intervention, and return results for use by decision-makers. However, it should be clearly understood that the scope of this disclosure is not limited to only automated or robotic implementations, since one or more portions of the system 42 could be manually operated if desired.

Figure 7:
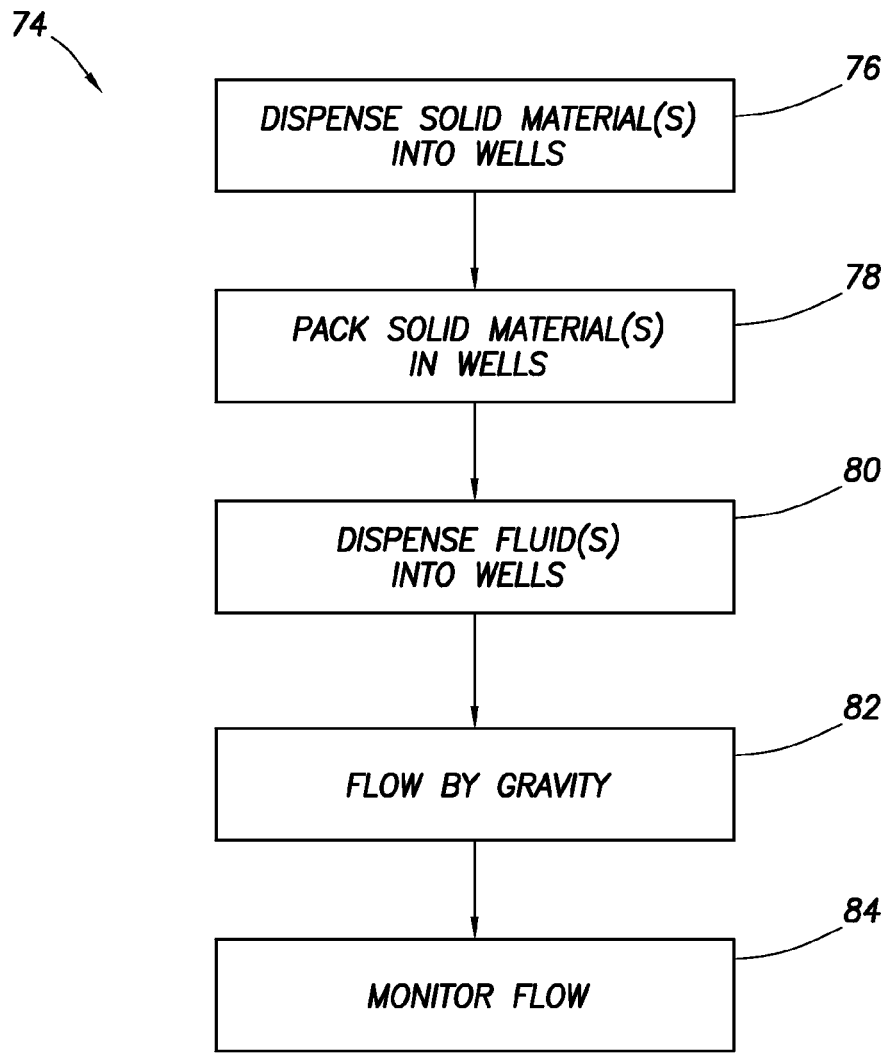
FIG. 7 is a representative flow chart for an example method that can embody the principles of this disclosure.

Referring additionally now to FIG. 7, an example of a method 74 that can embody the principles of this disclosure is representatively illustrated in flowchart form. The method 74 may be used with the system 42 examples described above, or the method may be used with other systems.

In step 76, one or more solid materials is/are dispensed into wells 38 of a filter plate 36. In the system 42, such solid materials could comprise formation particles 44 (e.g., formation cuttings collected during drilling), proppant 34 and/or mixtures thereof. However, the scope of this disclosure is not limited to use of any particular solid material(s) or combination of solid materials.

In step 78, the solid material(s) are packed in the wells 38. This packing step eliminates voids in the solid material, so that the solid material forms a consistent column of material in each well 38 through which liquid may be flowed.

Various means of packing the solid material can be used. In one example, the filter plate 36 can be centrifuged after the solid material is dispensed into the wells 38. In another example, the liquid 46 can be drawn with vacuum assist through the solid material after it has been dispensed into the wells 38. Thus, the scope of this disclosure is not limited to any particular technique for packing the solid material in the wells 38.

In step 80, one or more fluid(s) is/are dispensed into the wells 38. The FIG. 7 flowchart depicts this step 80 as being performed after the solid material is dispensed into and packed in the wells 38. However, in some examples, the fluid could be dispensed into the wells 38 prior to the solid material being dispensed into the wells.

In the example of FIGS. 3-5, a liquid 46 (such as, formation water, a potassium chloride solution or flowback water) may be dispensed into the wells 38 prior to or after the solid material(s) (such as, formation particles 44 and/or proppant 34) are dispensed into the wells. After the liquid 46 has flowed out of the filter plate 36, additional liquids (such as, fracturing fluid 30 and formation hydrocarbons 56) are flowed through the solid material(s) in the wells 38.

In step 82, fluids flow by gravity from the filter plate 36. In the examples described above and depicted in FIG. 5, the fracturing fluid 30 and formation hydrocarbons 56 flow only by force of gravity through the formation particles 44 and proppant 34 in the wells 38. Such flow of the fracturing fluid 30 and hydrocarbons 56 is not assisted by vacuum or by centrifugation.

In step 84, the flow of fluid(s) from the filter plate 36 is monitored during the test. In the examples described above, a volume and/or mass of the fluid collected in the wells 52 of the collection plate 50 is measured at multiple times during the test. Such measurements may be taken at regular time intervals or at selected times dependent on certain factors (such as, occurrence of hydrocarbon breakthrough, etc.).

In some examples, it may not be necessary to measure a volume or mass of the fluid collected in the wells 52 of the collection plate 50 at multiple times during the test. For example, it may in some instances be desired only to detect when hydrocarbon breakthrough occurs for each well 38, in which case hydrocarbon monitoring (such as, using a UV-VIS spectrometer) may be performed without also monitoring the volume or mass of the collected fluid.

The solid materials, liquids, combinations thereof and plates can be heated to a selected temperature (such as, a downhole temperature or another elevated temperature, for example, to enhance mobility of viscous hydrocarbons) throughout the entire method 74, or at any points during the method. Alternatively, the method 74 may be performed with some or all of the solid materials, liquids, combinations thereof and plates at ambient temperature.

It may now be fully appreciated that the above disclosure provides significant advances to the art of column flow testing. In examples described above, fracturing fluid 30 selection (including components such as surfactants, gels, biocides, clay stabilizers, gel breakers, etc., and combinations and ratios thereof) can be optimized for use with a particular formation 28 and/or proppant 34, and this optimization can be performed relatively quickly, efficiently and accurately using the flow testing system 42.

In particular, the above disclosure provides to the art a method 74 of flow testing. In one example, the method 74 can comprise: dispensing at least one solid material (such as, proppant 34 and/or formation particles 44) and at least one liquid (such as, fracturing fluid 30, liquid 46, hydrocarbons 56) into each of multiple wells 38 in a filter plate 36; and allowing the liquid to flow from the filter plate only by force of gravity.

The liquid can comprise a liquid hydrocarbon 56. The liquid hydrocarbon 56 may be oil and/or liquid gas.

The solid material may be dispensed into the wells 38 before or after the liquid is dispensed into the wells.

The method 74 may include heating the solid material and the liquid prior to the dispensing step. The method 74 may include heating the filter plate 36 after the dispensing step.

The method 74 can comprise flowing at least one of formation water and potassium chloride solution through the solid material, after the solid material is dispensed into the wells 38 and before the liquid is dispensed into the wells.

The method 74 may include measuring at multiple times, and for each of the wells 38, a quantity of the liquid flowed from the filter plate 36.

The fracturing fluid 30 composition may comprise at least one of a surfactant, a gel, a biocide, a clay stabilizer and a gel breaker.

The "at least one" liquid can include multiple fracturing fluid 30 compositions, and the method can include selecting one of the fracturing fluid compositions for use in a subterranean well fracturing operation based on the step of allowing the liquid to flow from the filter plate 36 only by force of gravity. The method can include introducing the selected fracturing fluid 30 composition into an earth formation 28, and fracturing the earth formation 28 using the selected fracturing fluid 30 composition.

A flow testing system 42 is also provided to the art by the above disclosure. In one example, the system 42 can comprise: a multiple well 38 filter plate 36, each of the wells having disposed therein a selected combination of formation particles 44, a fracturing fluid 30 composition and a liquid hydrocarbon 56; and a collection plate 50 vertically below the filter plate 36. The fracturing fluid 30 composition and the liquid hydrocarbon 56 flow from the filter plate 36 to the collection plate 50 only by force of gravity.

The formation particles 44, the fracturing fluid 30 composition and the liquid hydrocarbon 56 are heated to an elevated temperature.

The system 42 can include a measurement device 68 that measures at multiple times and for each of the wells 38 a quantity of the fracturing fluid 30 composition and the liquid hydrocarbon 56 flowed from the filter plate 36.

The system 42 can include a control system 60 that controls a robotic solid dispenser 62 that dispenses the formation particles 44 into the wells 38. The control system 60 may control a robotic liquid dispenser 64 that dispenses into the wells 38 at least one of the fracturing fluid 30 composition and the liquid hydrocarbon 56.

The fracturing fluid 30 composition may be selected for use in a fracturing operation in a subterranean well based on the flow from the filter plate 36 to the collection plate 50 only by force of gravity. The selected fracturing fluid 30 composition can be introduced into an earth formation 28, and the earth formation 28 can be fractured using the selected fracturing fluid 30 composition.

Although various examples have been described above, with each example having certain features, it should be understood that it is not necessary for a particular feature of one example to be used exclusively with that example. Instead, any of the features described above and/or depicted in the drawings can be combined with any of the examples, in addition to or in substitution for any of the other features of those examples. One example's features are not mutually exclusive to another example's features. Instead, the scope of this disclosure encompasses any combination of any of the features.

Although each example described above includes a certain combination of features, it should be understood that it is not necessary for all features of an example to be used. Instead, any of the features described above can be used, without any other particular feature or features also being used.

It should be understood that the various embodiments described herein may be utilized in various orientations, such as inclined, inverted, horizontal, vertical, etc., and in various configurations, without departing from the principles of this disclosure. The embodiments are described merely as examples of useful applications of the principles of the disclosure, which is not limited to any specific details of these embodiments.

In the above description of the representative examples, directional terms (such as "above," "below," "upper," "lower," etc.) are used for convenience in referring to the accompanying drawings. However, it should be clearly understood that the scope of this disclosure is not limited to any particular directions described herein.

The terms "including," "includes," "comprising," "comprises," and similar terms are used in a non-limiting sense in this specification. For example, if a system, method, apparatus, device, etc., is described as "including" a certain feature or element, the system, method, apparatus, device, etc., can include that feature or element, and can also include other features or elements. Similarly, the term "comprises" is considered to mean "comprises, but is not limited to."

Of course, a person skilled in the art would, upon a careful consideration of the above description of representative embodiments of the disclosure, readily appreciate that many modifications, additions, substitutions, deletions, and other changes may be made to the specific embodiments, and such changes are contemplated by the principles of this disclosure. For example, structures disclosed as being separately formed can, in other examples, be integrally formed and vice versa. Accordingly, the foregoing detailed description is to be clearly understood as being given by way of illustration and example only, the spirit and scope of the invention being limited solely by the appended claims and their equivalents.

What is claimed is:

1. A method of flow testing, comprising:
   dispensing a solid material and a liquid into each well of a multiple well filter plate, wherein each liquid comprises a fracturing fluid composition and at least two wells of the multiple wells contain different fracturing fluid compositions;
   allowing the liquids to flow from the wells in the filter plate only by force of gravity;
   measuring for each well at least one of a flow rate of the respective fracturing fluid composition flowing from the well or an amount of the respective fracturing fluid composition that flowed from the well; and selecting one of the fracturing fluid compositions for use in a subterranean well fracturing operation based on at least one of the flow rates of the fracturing fluid compositions or the amounts of the fracturing fluid compositions flowed from the wells.

2. The method of claim 1, wherein at least one of the liquids comprises a liquid hydrocarbon.

3. The method of claim 2, wherein the liquid hydrocarbon is selected from the group consisting of oil and liquid gas.

4. The method of claim 1, wherein the solid material is dispensed into the wells before the liquids are dispensed into the wells.

5. The method of claim 1, wherein the liquids are dispensed into the wells before the solid material is dispensed into the wells.

6. The method of claim 1, further comprising heating the solid material and the liquids prior to the dispensing.

7. The method of claim 1, further comprising heating the filter plate after the dispensing.

8. The method of claim 1, further comprising flowing at least one of the group consisting of formation water and potassium chloride solution through the solid material, after the solid material is dispensed into the wells and before the liquid is dispensed into the wells.

9. The method of claim 1, wherein the solid material is selected from the group consisting of proppant and formation particles.

10. The method of claim 1, further comprising measuring at multiple times and for each of the wells a quantity of the liquid flowed from the filter plate.

11. The method of claim 1, wherein each of the fracturing fluid compositions comprises at least one of the group consisting of a surfactant, a gel, a biocide, a clay stabilizer and a gel breaker.

12. The method of claim 1, further comprising: introducing the selected fracturing fluid composition into an earth formation; and fracturing the earth formation using the selected fracturing fluid composition.

13. A flow testing system, comprising:
a multiple well filter plate, each of the wells having disposed therein a selected combination of formation particles, fracturing fluid compositions, and a liquid hydrocarbon, wherein at least two wells of the multiple well filter plate contain different fracturing fluid compositions; and
a collection plate vertically below the filter plate, wherein the fracturing fluid composition and the liquid hydrocarbon flow from the filter plate to the collection plate only by force of gravity.

14. The system of claim 13, wherein the liquid hydrocarbon is selected from the group consisting of oil and liquid gas.

15. The system of claim 13, wherein the formation particles, the fracturing fluid composition and the liquid hydrocarbon are heated to an elevated temperature.

16. The system of claim 13, further comprising a measurement device that measures at multiple times and for each of the wells a quantity of the fracturing fluid composition and the liquid hydrocarbon flowed from the filter plate.

17. The system of claim 13, wherein the fracturing fluid composition comprises at least one of the group consisting of a surfactant, a gel, a biocide, a clay stabilizer and a gel breaker.

18. The system of claim 13, further comprising a control system that controls a robotic solid dispenser that dispenses the formation particles into the wells.

19. The system of claim 13, further comprising a control system that controls a robotic liquid dispenser that dispenses into the wells at least one of the group consisting of the fracturing fluid composition and the liquid hydrocarbon.

20. The system of claim 13, further comprising proppant in each of the wells in the filter plate.

\* \* \* \* \*